US012601707B2

(12) United States Patent
Chen et al.

(10) Patent No.: US 12,601,707 B2
(45) Date of Patent: Apr. 14, 2026

(54) SYMMETRIC STRUCTURAL TYPE OXYGEN SENSOR CHIP AND MANUFACTURING METHOD THEREOF

(71) Applicant: SUZHOU INDUSTRIAL PARK FUTES AUTOMOTIVE ELECTRONICS CO., LTD, Suzhou (CN)

(72) Inventors: Ronglang Chen, Wenzhou (CN); Loufu Luo, Suzhou (CN); Shikang Feng, Wenzhou (CN)

(73) Assignee: SUZHOU INDUSTRIAL PARK FUTES AUTOMOTIVE ELECTRONICS CO., LTD, Suzhou (CN)

( * ) Notice: Subject to any disclaimer, the term of this patent is extended or adjusted under 35 U.S.C. 154(b) by 83 days.

(21) Appl. No.: 18/600,436

(22) Filed: Mar. 8, 2024

(65) Prior Publication Data

US 2025/0123235 A1 Apr. 17, 2025

Related U.S. Application Data

(63) Continuation of application No. PCT/CN2024/072433, filed on Jan. 16, 2024.

(30) Foreign Application Priority Data

Oct. 11, 2023 (CN) .......................... 202311314202.9

(51) Int. Cl.
*G01N 27/409* (2006.01)
*G01N 27/407* (2006.01)
*G01N 33/00* (2006.01)

(52) U.S. Cl.
CPC ....... *G01N 27/409* (2013.01); *G01N 27/4071* (2013.01); *G01N 33/0036* (2013.01)

(58) Field of Classification Search
CPC ............. G01N 27/4071; G01N 27/409; G01N 33/0036
See application file for complete search history.

(56) References Cited

U.S. PATENT DOCUMENTS 5,635,120 A 6/1997 Long et al.
2019/0010852 A1* 1/2019 Quigley .................... F01N 9/00

FOREIGN PATENT DOCUMENTS

CN 100380117 C * 4/2008 .......... G01N 27/419
CN 102608182 A 7/2012
(Continued)

*Primary Examiner* — Kristina M Deherrera
*Assistant Examiner* — Gedeon M Kidanu
(74) *Attorney, Agent, or Firm* — Westbridge IP LLC

(57) ABSTRACT

Disclosed are a symmetric structural type oxygen sensor chip and its manufacturing method. The chip comprises a substrate layer, an insulating layer, and a heater layer; the substrate layer and the insulating layer constitute a tightly combined symmetrical structure with the heater layer as the axis of symmetry, no matter in the stress release during the sintering and forming process, or in the thermal expansion and contraction stress release during the subsequent use process, a relatively symmetrical and uniform stress release can be formed, the warpage of the chip is greatly improved, and the deformation of the chip can be basically controlled within 0.1 mm, which greatly reduces the chipping phenomenon during the assembly process, and can also reduce the cracking phenomenon during the use process.

6 Claims, 6 Drawing Sheets

(56)         References Cited

FOREIGN PATENT DOCUMENTS

| CN | 102680553 | A |   | 9/2012 |
|----|-----------|---|---|--------|
| CN | 102798653 | A |   | 11/2012 |
| CN | 104142363 | A |   | 11/2014 |
| CN | 104251876 | A |   | 12/2014 |
| CN | 104880500 | A |   | 9/2015 |
| CN | 205808981 | U |   | 12/2016 |
| CN | 111257392 | A |   | 6/2020 |
| CN | 111521648 | A |   | 8/2020 |
| CN | 213813441 | U | * | 7/2021 |
| JP | 2000292406 | A |   | 10/2000 |
| JP | 2003227810 | A |   | 8/2003 |
| JP | 2003279531 | A |   | 10/2003 |
| JP | 2003344348 | A |   | 12/2003 |
| JP | 2004085494 | A |   | 3/2004 |
| JP | 2005077127 | A |   | 3/2005 |
| KR | 20150007873 | A |   | 1/2015 |
| WO | 2018064888 | A1 |   | 4/2018 |

* cited by examiner

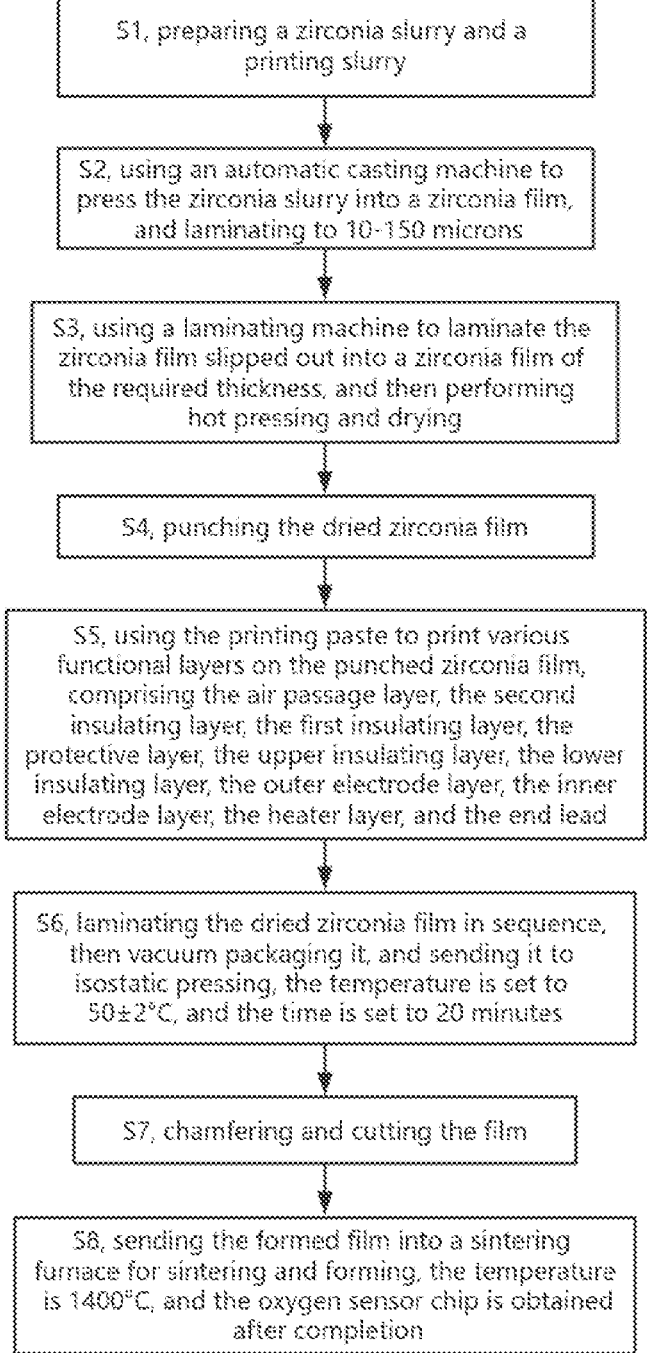

S1, preparing a zirconia slurry and a printing slurry

S2, using an automatic casting machine to press the zirconia slurry into a zirconia film, and laminating to 10-150 microns S3, using a laminating machine to laminate the zirconia film slipped out into a zirconia film of the required thickness, and then performing hot pressing and drying S4, punching the dried zirconia film S5, using the printing paste to print various functional layers on the punched zirconia film, comprising the air passage layer, the second insulating layer, the first insulating layer, the protective layer, the upper insulating layer, the lower insulating layer, the outer electrode layer, the inner electrode layer, the heater layer, and the end lead S6, laminating the dried zirconia film in sequence, then vacuum packaging it, and sending it to isostatic pressing, the temperature is set to 50±2°C, and the time is set to 20 minutes S7, chamfering and cutting the film S8, sending the formed film into a sintering furnace for sintering and forming, the temperature is 1400°C, and the oxygen sensor chip is obtained after completion

FIG.6

SYMMETRIC STRUCTURAL TYPE OXYGEN SENSOR CHIP AND MANUFACTURING METHOD THEREOF

CROSS-REFERENCE TO RELATED APPLICATIONS

This application is a continuation of International Application No. PCT/CN2024/072433, filed on Jan. 16, 2024, which claims priority to Chinese Patent Application No. 202311314202.9, filed on Oct. 11, 2023. All of the aforementioned applications are incorporated herein by reference in their entireties.

TECHNICAL FIELD

The present disclosure relates to the technical field of oxygen sensors, and in particular, to a symmetric structural type oxygen sensor chip and a manufacturing method thereof.

BACKGROUND

The oxygen sensor is an indispensable part in the control system of the electronic fuel injection engine, and is a key part for controlling the exhaust emission of an automobile, reducing the environmental pollution of the automobile and improving the combustion quality of the automobile engine. The chip functions as a core component of the oxygen sensor, and it is important to improve the quality of the chip.

The existing chip-type oxygen sensor chip production technology is of a three-layer structure, namely an alumina insulating layer wrapping a heater is positioned between the second and third zirconia matrix layers. Because different materials exist between the bonding parts of all layers, the shrinkage mismatch problem can occur due to the different shrinkage rates of the materials, so that serious layering, cracking or extremely low yield can be caused; or because the materials of the joint part are different, the high-temperature melting performance of the joint part has quite large difference, the sintering temperature is too high and easy to excessively melt, and the bonding is unstable when the sintering temperature is too low, so that serious layering, cracking and even falling are caused.

When the chip is sintered and formed at a high temperature of 1450 degrees, due to the different shrinkage rates of alumina and zirconia at high temperatures, it is easy to cause natural bending of the chip, which affects the number of finished chips. Therefore, it is of great practical significance to improve the natural cracking of sintering bending and thermal expansion and contraction in chip processing.

SUMMARY

In view of the above technical problems, the present application provides a symmetric structural type oxygen sensor chip, comprising: a substrate layer, an insulating layer, and a heater layer. The substrate layer and the insulating layer take the position of the heater layer as a symmetry axis to form a tightly combined symmetry structure, and the heater layer is wrapped in the middle; the substrate layer comprises four layers, namely a first substrate layer, a second substrate layer, a third substrate layer, and a fourth substrate layer from top to bottom; the insulating layer comprises an upper insulating layer and a lower insulating layer, both of which are provided between the second substrate layer and the third substrate layer; the heater layer is provided between the upper insulating layer and the lower insulating layer.

The present application adopts a symmetric structural chip structure, which is committed to improving the verticality of the chip. The embryos of traditional oxygen sensor chips are mostly three-layer structures, including three substrate layers, and then two insulating layers are provided between the two substrate layers below to wrap a heater layer. The insulating layer generally adopts an alumina insulating layer, and the zirconia substrate layer and the alumina insulating layer have different shrinkage rates at high temperatures. This three-layer asymmetric structure is prone to bending deformation in one direction during the sintering process due to uneven stress, and it is also prone to cracking during thermal expansion and contraction, resulting in a high rate of defective products. The four-layer structure of the present application achieves axial symmetry in the vertical direction. During high-temperature sintering and cooling, the stress from the top and bottom offsets each other, and even the deformation caused by repeated heating has relatively symmetrical shrinkage, which can effectively improve the natural bending and cracking during chip processing, and obtain a higher product qualification rate.

Preferably, an air passage layer is provided above the second substrate layer. An outer electrode layer is provided on the upper surface of the first substrate, an inner electrode layer is provided between the first substrate layer and the second substrate layer, and a protective layer for isolating gas and protecting the outer electrode layer is provided on the top of the outer electrode layer. A first insulating layer is provided between the first substrate layer and the outer electrode layer, a terminal lead is provided on the outer side of the fourth substrate layer, and a second insulating layer is provided between the terminal lead and the fourth substrate layer.

Preferably, the substrate layer is a zirconia film containing mullite and alumina.

Preferably, the insulating layer is an alumina insulating layer.

Preferably, the inner electrode layer and the outer electrode layer are platinum electrodes plate.

A manufacturing method for a symmetric structural type oxygen sensor chip comprises:

S1, preparing zirconia slurry and printing slurry;

S2, using an automatic casting machine to press the zirconia slurry into a zirconia film, and laminating it to 10-150 microns;

S3, using a laminator to laminate the casted zirconia film into a zirconia film of the required thickness, and then hot pressing and drying;

S4, punching the dried zirconia film;

S5, using the printing paste to print various functional layers on the punched zirconia film, including the air passage layer, the second insulating layer, the first insulating layer, the protective layer, the upper insulating layer, the lower insulating layer, the outer electrode layer, the inner electrode layer, the heater layer, and the end lead;

S6, laminating the dried zirconia film in sequence, then vacuum-packing it, and sending it for isostatic pressing, the temperature is set to 50±2° C., and the time is set to 20 minutes;

S7, chamfering and cutting the film;

S8, sending the formed film into a sintering furnace for sintering and forming, the temperature is 1400° C., and the oxygen sensor chip is obtained after completion.

Preferably, the zirconia slip is composed of nano-grade yttria-stabilized zirconia slip powder and auxiliary materials. The auxiliary materials include a dispersant, an organic solvent, a binder, and an adhesive.

Preferably, the zirconia slip includes 50-60% of 5 mol yttria-stabilized zirconia slip powder, 20-30% of the dispersant and organic solvent, 10-15% of the binder, and 20-25% of the adhesive.

The prior art mostly uses 3 mol or 8 mol yttria-stabilized zirconia, which can produce stable tetragonal and cubic phases at room temperature. However, the present application uses 5 mol yttria-stabilized zirconia, which can retain the tetragonal and cubic phases in the microstructure. The tetragonal phase has excellent fracture toughness, hardness, and strength. Maintaining the stability of the tetragonal phase during processing and manufacturing can effectively ensure the processing effect of the film. In addition, the tetragonal phase zirconia has higher catalytic activity.

The experimental spectra of ultraviolet Raman, XRD, and visible Raman of yttria-stabilized zirconia show that although the addition of yttria stabilizer can make the tetragonal phase exist in the bulk phase, the tetragonal phase on the surface is not stable and is easily transformed into a monoclinic phase, especially when the stabilizer content is low, the tetragonal phase is almost invisible on the surface, and the surface is all monoclinic phase. However, when the content of yttria stabilizer is high, such as 8 mol, cubic phase zirconia is easily generated, so the present application uses 5 mol yttria-stabilized zirconia.

The organic solvent includes one or more of polyvinyl alcohol (PVA), polyethylene glycol (PEG), polyacrylic acid (PAA), camphor, stearic acid, and glycerol. The addition of volatile organic compounds can promote the compaction of ultrafine powders.

The binder is one or more of melamine resin and acrylic resin.

The dispersant is one or more of fish oil, castor oil, triethanolamine, and polyacrylic acid.

In addition to the above formula, when preparing the slip, the present application also adds alkoxide to improve the contact between adjacent grains, facilitate compact compaction, and form a transient liquid phase through rapid diffusion of particles. A limited amount of alkoxide will exist at the grain boundary. The liquid phase can promote particle rearrangement and improve the uniformity of pressure transmission between particles. In the subsequent sintering process, it can help the film to be less prone to cracking and easier to sinter.

The present application also uses a sintering aid in the sintering process. The sintering aid includes one or more of oxides and fluorides of alkali metals, alkaline earth metals, boron, and bismuth. They are all volatile aids, which can be volatilized and eliminated without affecting the chemical properties of the final product.

The present application adopts a new technology of a symmetrical new four-layer structure, which is equivalent to two layers of zirconia substrate layers sandwiched between two layers of insulating layers, and the center is wrapped with a heater layer, which is the heat source. It is a symmetrical structure centered on the heater. Whether it is the stress release during the sintering and forming process or the thermal expansion and contraction stress release during the subsequent use process, a relatively symmetrical and uniform stress release can be formed, and the curvature of the chip is greatly improved. The deformation of the chip can be controlled within 0.1 mm, which greatly reduces the phenomenon of chip breakage during the assembly process and can also reduce the phenomenon of cracking during use.

The present application improves the formula of zirconia slip and obtains better flexural strength and fracture toughness.

BRIEF DESCRIPTION OF THE DRAWINGS

The following is a further description of the present application in conjunction with the accompanying drawings.

FIG. 6 is a flowchart of the present application.

DETAILED DESCRIPTION OF THE EMBODIMENTS

The following is a further detailed description of various aspects of the present application.

Unless otherwise defined or explained, all technical and scientific terms used herein have the same meaning as commonly understood by one of ordinary skill in the art. Furthermore, any methods and materials similar or equivalent to those described herein can be used in the practice or testing of the present application.

Figure 2:
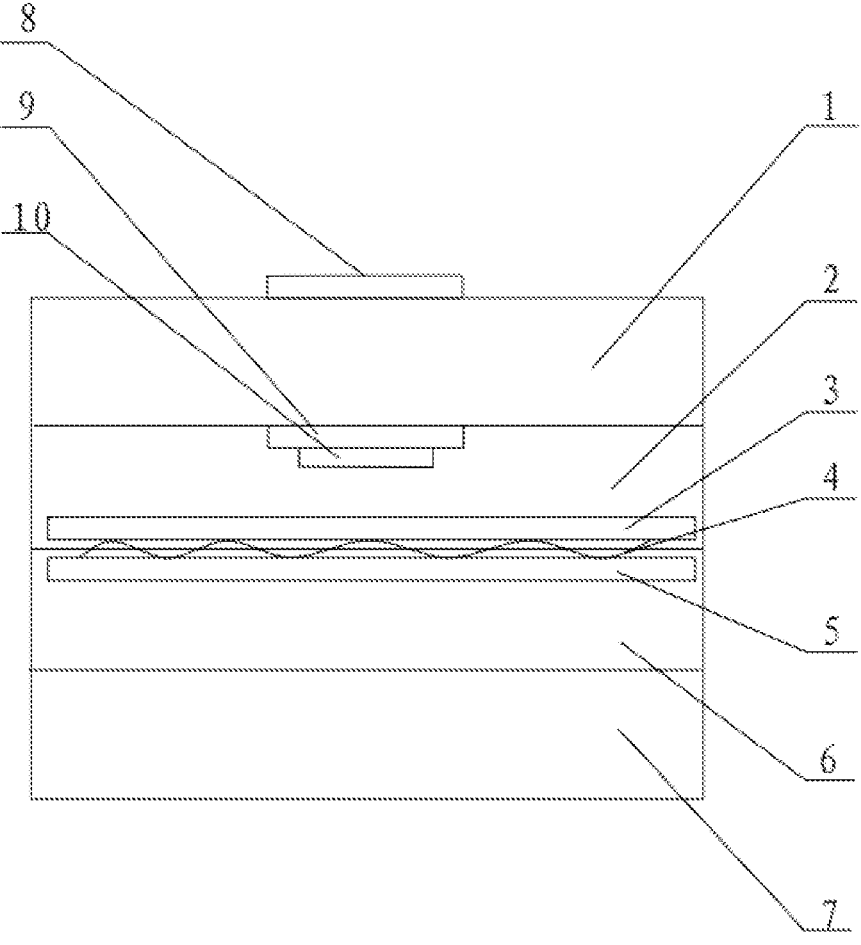
FIG. 2 is a schematic diagram of the structure of an oxygen sensor chip in the present application.
Figure 3:
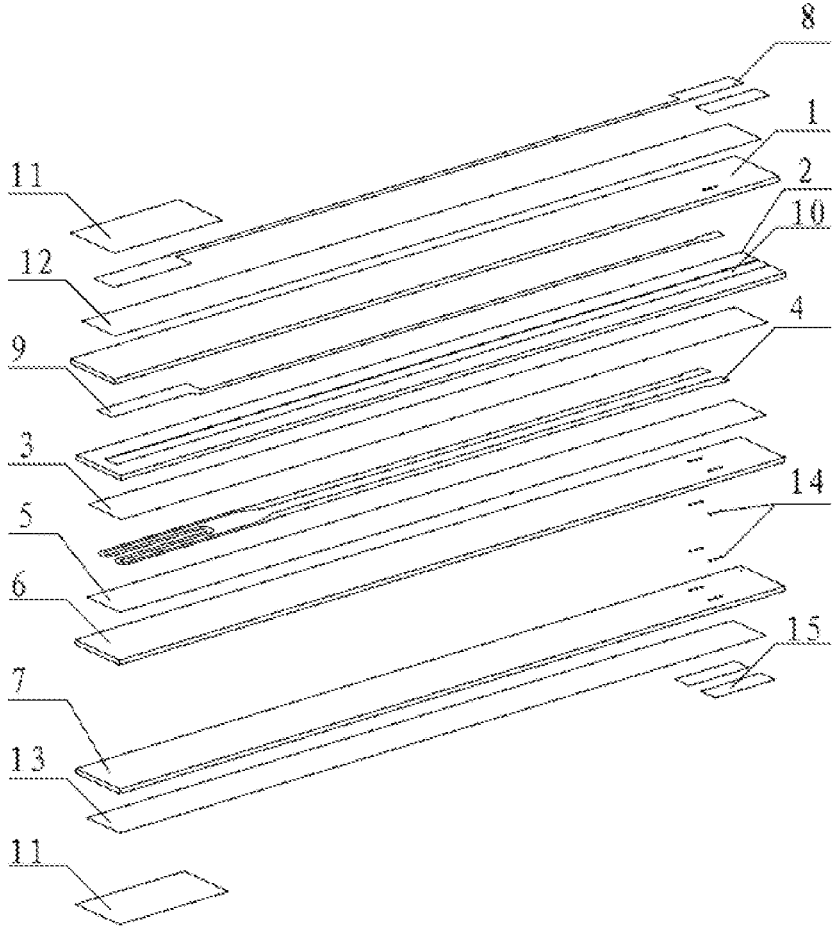
FIG. 3 is a schematic diagram of an embodiment of the present application.

As shown in FIGS. 2-3, the present application provides a symmetric structural type oxygen sensor chip, comprising: a substrate layer, an insulating layer, and a heater layer 4.

The substrate layer and the insulating layer take the position of the heater layer 4 as a symmetry axis to form a tightly combined symmetry structure, and the heater layer 4 is wrapped in the middle.

The substrate layer comprises four layers, which are the first substrate layer 1, the second substrate layer 2, the third substrate layer 6, and the fourth substrate layer 7 from top to bottom.

The insulating layer comprises an upper insulating layer 3 and a lower insulating layer 5, both of which are disposed between the second substrate layer 2 and the third substrate layer 6.

The heater layer 4 is disposed between the upper insulating layer 3 and the lower insulating layer 5.

Figure 1:
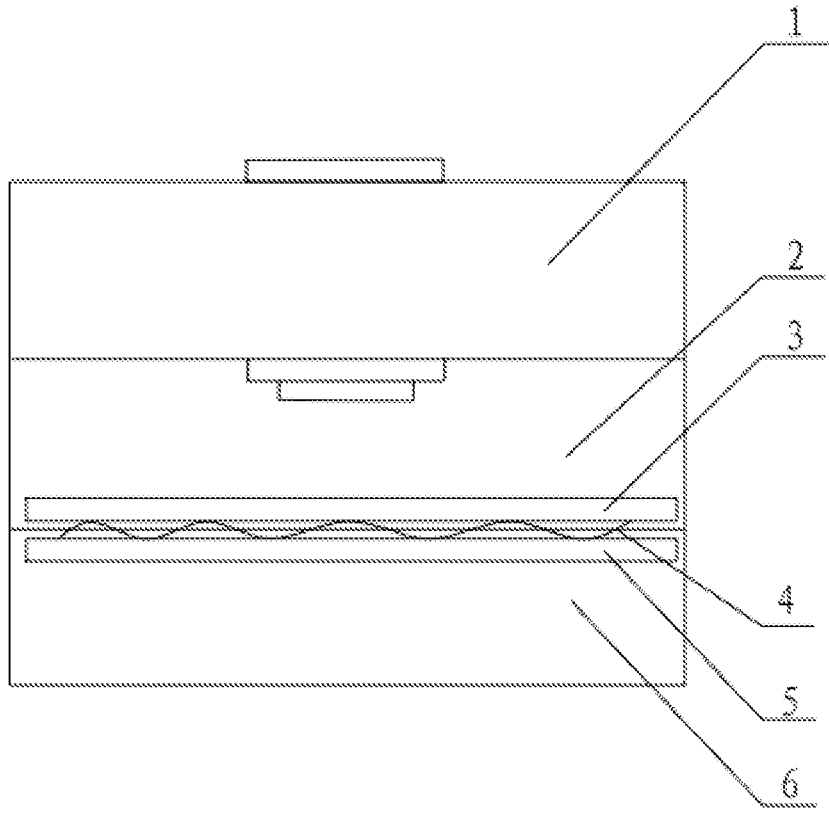
FIG. 1 is a schematic diagram of the structure of an oxygen sensor chip in the prior art.

The present application adopts a symmetrical chip structure design, which is committed to improving the verticality of the chip. As shown in FIG. 1, the embryo of the traditional oxygen sensor chip is mostly a three-layer structure, including three substrate layers, and then two insulating layers are disposed between the two substrate layers below, which are used to wrap a heater layer 4. The insulating layer is generally an alumina insulating layer. The zirconia substrate layer and the alumina insulating layer have different shrinkage rates at high temperatures. This three-layer asymmetric structure is prone to bending deformation in one direction due to uneven stress during the sintering process. It is also prone to cracking during thermal expansion and contraction, and the rate of defective products is high. The four-layer structure of the present application achieves axial symmetry in the vertical direction. During high-temperature sintering and cooling, the stress up and down is in contact with each other, and even the deformation caused by repeated heating is relatively symmetrical shrinkage, which can effectively improve the natural bending and cracking of the chip during processing and obtain a higher product qualification rate.

The upper side of the second substrate layer 2 is provided with an air passage layer 10, the upper surface of the first substrate is provided with an outer electrode layer 8, an inner electrode layer 9 is provided between the first substrate layer 1 and the second substrate layer 2, the top of the outer electrode layer 8 is provided with a protective layer 11 for isolating gas and protecting the outer electrode layer 8, a first insulating layer 12 is provided between the first substrate layer 1 and the outer electrode layer 8, and the outer side of the fourth substrate layer 7 is provided with a end lead 15, and a second insulating layer 13 is provided between the end lead 15 and the fourth substrate layer 7.

The present application takes into account that not only are there cracks and stress shocks during processing, but also in actual use, common engine failures are caused by sensor stress failure caused by thermal shock of the electrode layer. When the oxygen sensor chip is in use, especially when the temperature of water droplets in the gas is low in a low-temperature environment, the oxygen sensor needs to be quickly heated to the working temperature or the gas needs to be cooled. This alternating hot and cold process makes it easy to generate thermal shock, causing the chip layers to crack from some tiny defects. Yttria-stabilized zirconia has low thermal conductivity and high expansion coefficient. This characteristic determines that the zirconia film prepared from this material has a large temperature gradient. It is easier to crack at the defect under a high expansion coefficient. Therefore, the present application considers adding a second phase material with high thermal conductivity.

This second phase material can be one of alumina or mullite or a combination thereof, to increase the effective thermal conductivity of the film, improve the heat conduction performance, and accelerate the heat transfer between the inside and the outside, thereby reducing the crystal expansion and contraction during the temperature change process Size, not only can reduce cracking during use, but also reduce post-sintering cooling cracking, achieving the effect of killing two birds with one stone.

For the selection of mullite and alumina, after experiments, the present application suggests using mullite when used alone. Although the thermal conductivity of mullite is not as good as that of alumina, it is found after experiments that the elastic modulus and Poisson's ratio of mullite match better with 5 mol yttria-stabilized zirconia, and the resistance to thermal shock is better. Here, the present application also proposes that it is found in the experiment that adding a small amount of alumina (volume content <1.35%) can increase the conductivity of the zirconia film. It is found by comparative observation that this is because alumina can remove impurities between grain boundaries; adding a large amount of alumina can improve the thermal shock resistance, that is, the resistance to temperature changes, which is the effect of reducing cracks expected by the present application, but it will also lead to a decrease in conductivity, so the amount of alumina used needs to be further optimized by experiments.

Therefore, the substrate layer in the present application is a zirconia film containing mullite and alumina, the insulating layer is an alumina insulating layer, and the inner electrode layer 9 and the outer electrode layer 8 are platinum electrode plates.

As shown in FIG. 6, the present application also provides a method for manufacturing a symmetric structural type oxygen sensor chip, comprising:

S1, preparing zirconia slurry and printing slurry;

S2, using an automatic casting machine to press the zirconia slurry into a zirconia film, laminating it to 10-150 microns;

S3, using a laminator to laminate the casted zirconia film into a zirconia film of the required thickness, and then hot pressing and drying;

S4, punching the dried zirconia film;

S5, using printing slurry to print each functional layer on the punched zirconia film, including the airway layer 10, the second insulating layer 13, the first insulating layer 12, the protective layer 11, the upper insulating layer 3, the lower insulating layer 5, the outer electrode layer 8, the inner electrode layer 9, the heater layer 4, and the end lead 15;

S6, laminating the dried zirconia film in sequence, then vacuum packaging, and sending it to isostatic pressing, the temperature is set to 50±2° C., and the time is set to 20 minutes;

S7, chamfering and cutting the film;

S8, the formed film is sent to the sintering furnace for sintering and forming, the temperature is 1400° C., and the oxygen sensor chip is obtained after completion.

The zirconia slip is composed of nano-scale yttria-stabilized zirconia slip powder and auxiliaries, and the auxiliaries include a dispersant, an organic solvent, a binder, and an adhesive.

The zirconia slip includes 50-60% of 5 mol yttria-stabilized zirconia slip powder, 20-30% of dispersant and organic solvent, 10-15% of binder, and 10-25% of adhesive.

The prior art mostly uses 3 mol or 8 mol yttria-stabilized zirconia, which can produce stable tetragonal and cubic phases at room temperature. Since the tetragonal phase has excellent fracture toughness, hardness, and strength, maintaining the stability of the tetragonal phase during processing and manufacturing can effectively ensure the processing effect of the film. In addition, the tetragonal zirconia has higher catalytic activity. However, the present application uses 5 mol yttria-stabilized zirconia, which can retain the tetragonal and cubic phases in the microstructure. As can be seen from FIG. 5, 70-80 of the XRD peaks show a bimodal grain size distribution, and the tetragonal phase and the cubic phase coexist. Since the two have similar structures, the spectra are superimposed.

Experimental spectra of UV Raman, X-ray diffraction, and visible Raman of yttria-stabilized zirconia show that although the addition of yttria stabilizer can make the tetragonal phase exist in the bulk phase, the tetragonal phase on the surface is not stable and is easily transformed into a monoclinic phase, especially when the stabilizer content is low, the tetragonal phase is almost invisible on the surface, and the surface is all monoclinic phase, but when the yttria stabilizer content is high, such as 8 mol, cubic zirconia phase is easily generated, and the semi-permeability is poor. Taking all factors into account, this application chooses to use 5 mol yttria-stabilized zirconia.

Organic solvents include one or several combinations of polyvinyl alcohol (PVA), polyethylene glycol (PEG), polyacrylic acid (PAA), camphor, stearic acid, and glycerol. The addition of volatile organic compounds can promote the compaction of ultrafine powder.

The binder is a combination of one or several of melamine resin and acrylic resin.

The dispersant is a combination of one or several of fish oil, castor oil, triethanolamine, and polyacrylic acid.

When preparing the slip, this application can also appropriately add alkoxide to improve the contact between adjacent grains, facilitate close compaction, and form a transient liquid phase through rapid diffusion of particles. A limited amount of alkoxide will exist at the grain boundary, and the liquid phase can promote particle rearrangement.

The generated liquid has the best effect on particle rearrangement and pressure transmission uniformity, improves the uniformity of pressure transmission between particles, and helps the film to be less prone to cracking and easier to sinter in the subsequent sintering process.

This application also uses sintering aids in the sintering process. The sintering aids include a combination of one or several of oxides and fluorides of alkali metals, alkaline earth metals, boron, and bismuth, all of which are volatile aids that can volatilize and eliminate without affecting the chemical properties of the final product.

The experimental design of this application is committed to optimizing the content selection of mullite and alumina in zirconia slip. The experiment found that when the mullite content exceeds 20%, the intercrystalline phase decreases. Due to the decrease in yttrium content after reaction with the stabilizer yttria, the oxygen vacancy concentration decreases, resulting in a serious decrease in conductivity. The best choice is 5 mol yttria-stabilized zirconia+5% alumina+10% mullite (content by volume) slip, which has the best final sintering effect.

Among them, when the sintering aid is also bismuth oxide, under the condition of about 1400-1450° C., this application also carries out X-ray diffraction analysis on the sintered chip. It can be seen that no other crystal phases appear. In combination with the structural improvement and manufacturing method of this application, the cracking rate of the manufactured chip is greatly reduced, and the generated curvature is less than 0.1 mm, which has achieved a large increase in economic benefits.

The hardness, fracture toughness, and flexural strength test data of the final sintered chips with different formulas are shown in Table 1, where the average value of at least five samples of each formula is taken.

| (a-Alumina, b-Mullite) | Hardness(Gpa) | Fracture toughness (MPam1/2) | Flexural strength(Mpa) |
|---|---|---|---|
| 5 molYSZ | 12 ± 1.3 | 1.5 ± 0.3 | 185 ± 55 |
| 5 molYSZ + 5% a | 18 ± 1.5 | 2.2 ± 0.1 | 187 ± 23 |
| 5 molYSZ + 5% b | 15 ± 1.1 | 1.9 ± 0.3 | 203 ± 15 |
| 5 molYSZ + 10% a | 27 ± 1.3 | 3.5 ± 0.2 | 240 ± 11 |
| 5 molYSZ + 10% b | 23 ± 1.8 | 3.2 ± 0.1 | 220 ± 18 |
| 5 molYSZ + 5% a + 10% b | 25 ± 1.5 | 3.0 ± 0.2 | 223 ± 13 |

From the experimental data, it can be seen that the hardness, fracture toughness, and flexural strength of the chip finally sintered with 5 mol yttria-stabilized zirconia+5% alumina+10% mullite slip are all greatly improved compared with those obtained with only 5 mol yttria-stabilized zirconia. The hardness is increased by 108%, the fracture toughness is increased by 100%, and the flexural strength is increased by 20%. It is worth noting that in the case of adding alumina alone, the hardness and fracture toughness are both significantly improved, and the improvement efficiency is even higher than that of mullite with the same proportion and the simultaneous addition of 5% alumina and 10% mullite. However, this application also tested the grain boundary conductivity of different components and found that the conductivity loss caused by adding more than 5% alumina is too large. In the component with 5% alumina, the ionic conductivity decreases by 28%, and in the component with 10% alumina, the ionic conductivity decreases by 47%. The grain boundary conductivity decreases more seriously, so it is not adopted.

There are multiple embodiments of the present application. Two of them are listed here.

Embodiment 1

As shown in FIG. 3, the present application provides a symmetrical structure four-wire common switch type oxygen sensor chip and its manufacturing method.

This four-wire common switch type sensor chip includes from top to bottom: protection layer 11, outer electrode, first insulating layer 12, first substrate layer 1, inner electrode, air passage, second substrate layer 2, first insulating layer 12, heater layer 4, second insulating layer 13, third substrate layer 6, fourth substrate layer 7, second insulating layer 13, end lead 15 and protection layer 11.

Here are the steps to prepare a four-wire general-purpose oxygen sensor chip:

S1, preparing zirconia slurry and printing slurry;

zirconia slurry: 50-60% of 5 mol yttria-stabilized zirconia slurry powder (5% alumina+10% mullite), 20-30% of dispersant and organic solvent, 10-15% of binder, 20-25% of adhesive;

protective layer 11 printing slurry: 25-30% of alumina powder, 25-30% of starch, 2-5% of binder, 30-35% of organic solvent, 2-5% of plasticizer, 2-5% of dispersant;

insulating layer printing slurry: 40-50% of alumina powder, 5-10% of glass powder, 2-5% of binder, 30-40% of organic solvent, 2-5% of plasticizer, 2-5% of dispersant;

electrode layer printing slurry: 65-75% of platinum powder, 3-8% of oxide, 2-5% of binder, 10-20% of organic solvent;

air passage printing slurry: 40-50% of starch, 2-5% of binder, 40-50% of organic solvent, 2-5% of dispersant;

S2, using an automatic coater to press the zirconia slurry into a zirconia film, set the temperature to 40-60° C., and the thickness to 40±3 μm;

S3, using a laminating machine to laminate the casted zirconia film into a film with a thickness of 0.45±0.05 mm;

S4, hot-pressing the zirconia film after lamination, the hot-pressing temperature is 50° C., the hot-pressing pressure is 20 Mpa, and the hot-pressing time is 90 s. Then dry it at 100° C. for 2 hours. The thickness of the film after hot-pressing is about 0.42 mm;

S5, punching the dried zirconia film;

S6, printing the printing slurry on the perforated zirconia film, print the air passage, the second insulating layer 13, the first insulating layer 12, the protective layer 11, the first insulating layer 12, the second insulating layer 13, the outer electrode, the inner electrode, the heater layer 4, and the end lead 15, and fill the through holes 14 after perforation with slurry;

S7, drying the zirconia film after printing, the drying temperature is about 80° C., and the time is 4 minutes;

S8, laminating the dried zirconia film according to the symmetrical structure shown in FIG. 3;

S9, vacuum-packing the laminated film and send it for isostatic pressing, the temperature is about 50° C., and the time is about 20 minutes;

S10, chamfering and cutting the film, and the preliminary model of the chip is fully formed;

S11, sending the preliminary model of the chip to the sintering furnace for sintering and forming, the temperature is about 1430° C., and the chip is formed;

S12, inspecting 100 pieces of the sintered chips, and the bending degree of 100% of the chips is less than 0.1 mm.

Embodiment 2

The manufacturing method of the present application is also applicable to the processing of four-wire chip-type limiting current oxygen sensor chips.

The four-wire chip-type limiting current oxygen sensor is also called the four-wire air-fuel ratio sensor (A/F sensor) and is also called the wide-range oxygen sensor. Compared with the traditional switching type oxygen sensor, the switching type can only reflect whether the exhaust gas is rich or lean, while the A/F sensor can output specific exhaust gas air-fuel ratio data based on the detected current feedback. The ECU can accurately adjust the fuel injection according to the detected air-fuel ratio data to achieve the purpose of full combustion of the fuel.

The core component of the air-fuel ratio sensor is compared with the switching type, mainly by adding a gas diffusion layer. When a fixed voltage is applied to the two signal lines of the sensor, due to the influence of the diffusion layer limiting the gas diffusion, different atmospheres will generate different current outputs. According to the linear relationship between the current and the air-fuel ratio, the ECU can accurately feedback the air-fuel ratio.

Figure 4:
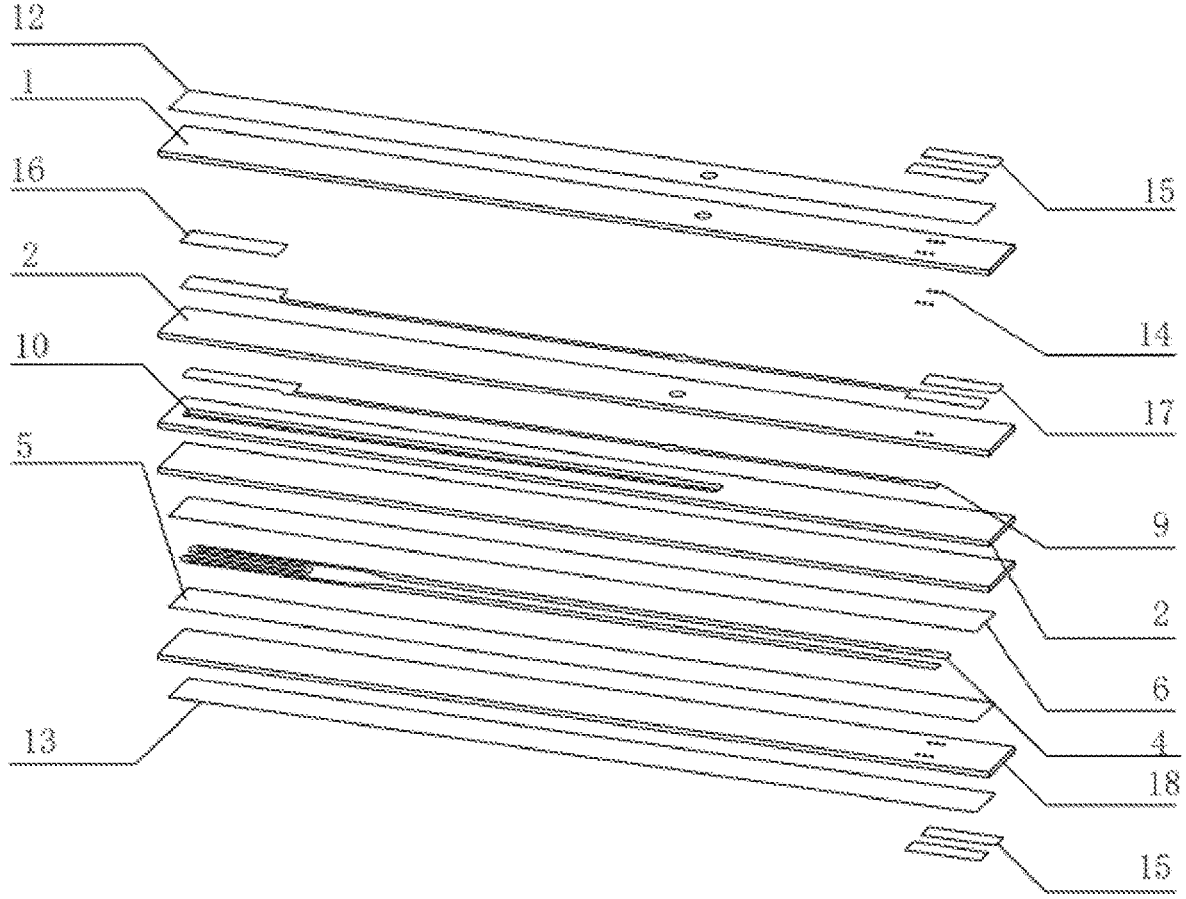
FIG. 4 is a schematic diagram of another embodiment of the present application.
Figure 5:
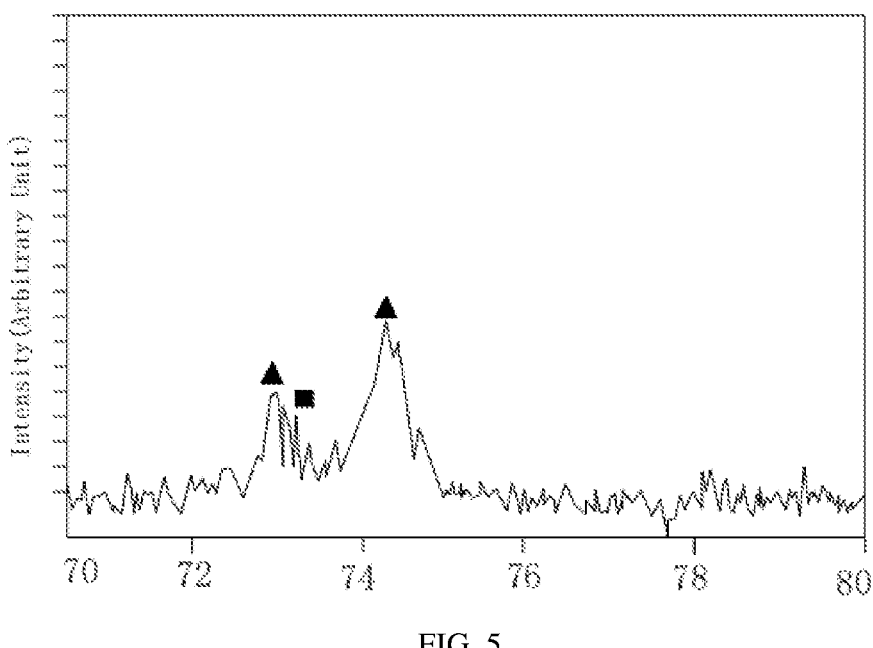
FIG. 5 is an X-ray diffraction analysis diagram of a 5 mol yttria-stabilized zirconia film.

As shown in FIG. 4, the four-wire chip-type limiting current oxygen sensor chip includes, from top to bottom, a end lead 15, a first insulating layer 12, a first substrate layer 1, a cavity 16, a pump electrode 17, a second substrate layer 2, an inner electrode, an air passage, a third substrate layer 6, a fourth substrate layer 7, an upper insulating layer 3, a heater layer 4, a lower insulating layer 5, a fifth substrate layer 18, a second insulating layer 13, and a end lead 15.

The four-wire chip-type limiting current oxygen sensor chip is prepared by the following steps:

S1, preparing zirconia slurry and printing slurry;

zirconia slurry: 50-60% of 5 mol yttria stabilized zirconia slurry powder (5% alumina+10% mullite), 20-30% of dispersant and organic solvent, 10-15% of binder, 20-25% of adhesive;

protective layer 11 printing slurry: 25-30% alumina powder, 25-30% raw powder, 2-5% binder, 30-35% organic solvent, 2-5% plasticizer, 2-5% dispersant;

insulating layer printing slurry: 40-50% alumina powder, 5-10% glass powder, 2-5% binder, 30-40% organic solvent, 2-5% plasticizer, 2-5% dispersant;

electrode layer printing slurry: 65-75% platinum powder, 3-8% oxide, 2-5% binder, 10-20% organic solvent;

diffusion layer printing slurry: 40-50% zirconia powder, 10-20% carbon black, 2-5% binder, 25-35% organic solvent, 2-5% plasticizer, 2-5% dispersant;

air passage printing slurry: 40-50% raw powder, 2-5% binder, 40-50% organic solvent, 2-5% dispersant;

S2, pressing the zirconia slurry into a zirconia film by an automatic casting machine, the temperature is 40-60 degrees, and the thickness is 40±3 μm;

S3, stacking the zirconia film rolled out by the laminator into a zirconia film with a thickness of 0.45±0.05 mm;

S4, heat pressing the zirconia film after lamination, the heat pressing temperature is 50° C., the heat pressing pressure is 20 Mpa, the heat pressing time is 90 s, and then dry it, the drying temperature is 100° C., the time is 2 h, and the thickness of the zirconia film after heat pressing is about 0.42 mm;

S5, punching the dried zirconia film, and using a punching machine to punch out the air passage, which is used for the large reference air passage of the inner electrode;

S6, printing on the punched zirconia film with printing slurry, print the air passage, terminal insulating, lead insulating, protective layer 11, first insulating layer 12, second insulating layer 13, outer electrode, inner electrode, diffusion cavity 16, heater layer 4 and end lead 15;

S7, drying the zirconia film after printing, the drying temperature is about 80° C., and the time is about 4 min;

S8, stacking the dried zirconia film in the order of FIG. 4;

S9, vacuum packing the film after lamination, and sending it to isostatic pressing, the temperature is about 50° C., and the time is about 20 min;

S10, chamfering and cutting the zirconia film, and the preliminary model of the chip is processed;

S11, sending the initially formed chip into the sintering furnace for sintering and forming, the temperature is 1400° C., and the chip is formed;

S12, 100 Pcs of the formed chips are inspected, and 100% of the chips have a curvature of less than 0.1 mm.

In addition, the present application also tried to use flash sintering (FS) technology in the sintering stage, which shortened the sintering time and reduced the sintering temperature. However, during this process, the present application found that the conductivity of the oxygen sensor chip produced under the same conditions and manufacturing method was greater than that of the chip produced by the traditional sintering technology. It is speculated that this is because the concentration of oxygen vacancies was increased during the flash sintering process, and both the ionic conductivity and the electronic conductivity were increased. However, after the flash sintering, the electronic conductivity was restored to its original state, only the ionic conductivity was increased, and the increment of the electronic conductivity was not retained. In addition, it was observed that the surface of the chip turned black during the flash sintering process. After the DC voltage was removed, the surface blackening phenomenon disappeared, which may be related to the change of the electronic conductivity. The increment of the ionic conductivity was still maintained after the sintering was completed. It is speculated that this may be due to the grain boundary defects that occurred during the sintering process. The impact on the chip life during subsequent use is still unknown, so it is only proposed as a point of view and is not one of the specific embodiments of the present application.

The above description is only a specific embodiment of the present application, but the protection scope of the present application is not limited to this. Any person skilled in the art can easily conceive of changes or substitutions within the technical scope disclosed by the present application, which should all be covered by the protection scope of the present application. Therefore, the protection scope of the present application should be based on the protection scope of the claims.

What is claimed is:

1. A symmetric structural type oxygen sensor chip, comprising:

a substrate layer, an insulating layer, and a heater layer; wherein the substrate layer and the insulating layer take the position of the heater layer as a symmetry axis to form a tightly combined symmetry structure, encapsulating the heater layer in a middle;

the substrate layer comprises four layers, from top to bottom, a first substrate layer, a second substrate layer, a third substrate layer, and a fourth substrate layer;

the insulating layer comprises an upper insulating layer and a lower insulating layer, both of which are disposed between the second substrate layer and the third substrate layer;

the heater layer is disposed between the upper insulating layer and the lower insulating layer;

an air passage layer is disposed above the second substrate layer, an outer electrode layer is disposed on a upper surface of the first substrate layer, an inner electrode layer is disposed between the first substrate layer and the second substrate layer, a protective layer for isolating gas and protecting the outer electrode layer is disposed on a top of the outer electrode layer, a first insulating layer is disposed between the first substrate layer and the outer electrode layer, a end lead is disposed on an outer side of the fourth substrate layer, and a second insulating layer is disposed between the end lead and the fourth substrate layer;

the substrate layer is a zirconia film containing mullite and alumina, the zirconia film is pressed from zirconia slip, wherein the zirconia slip contains alumina with a volume content of 5% and mullite with a volume content of 10%; and the insulating layer is an alumina insulating layer.

2. The symmetric structural type oxygen sensor chip according to claim 1, wherein the inner electrode layer and the outer electrode layer are platinum electrode plates.

3. A method for manufacturing a symmetric structural type oxygen sensor chip according to claim 2, comprising:

S1, preparing a zirconia slurry and a printing slurry;

S2, using an automatic casting machine to press the zirconia slurry into a zirconia film, and laminating to 10-150 microns;

S3, using a laminating machine to laminate the zirconia film slipped out into a zirconia film of the required thickness, and then performing hot pressing and drying;

S4, punching the dried zirconia film;

S5, using the printing paste to print various functional layers on the punched zirconia film, comprising the air passage layer, the second insulating layer, the first insulating layer, the protective layer, the upper insulating layer, the lower insulating layer, the outer electrode layer, the inner electrode layer, the heater layer, and the end lead;

S6, laminating the dried zirconia film in sequence, then vacuum packaging it, and sending it to isostatic pressing, the temperature is set to $50\pm2°$ C., and the time is set to 20 minutes;

S7, chamfering and cutting the film; and

S8, sending the formed film into a sintering furnace for sintering and forming, the temperature is $1400°$ C., and the oxygen sensor chip is obtained after completion.

4. The method according to claim 3, wherein the zirconia slip is composed of nano-grade yttria stabilized zirconia slip powder, and auxiliary materials, the auxiliary materials comprise a dispersant, an organic solvent, a binder, and an adhesive.

5. The method according to claim 4, wherein the zirconia slip comprises 50-60% of 5 mol yttria stabilized zirconia slip powder, 20-30% of dispersant and organic solvent, 10-15% of binder, and 20-25% of adhesive.

6. The method according to claim 5, wherein:

the organic solvent comprises one or a combination of more of polyvinyl alcohol, polyethylene glycol, polyacrylic acid, camphor, stearic acid, and glycerol; the dispersant is one or or a combination of more of fish oil, castor oil, triethanolamine, and polyacrylic acid; the binder is one or several combinations of melamine resin and acrylic resin.

\* \* \* \* \*